(12) United States Patent
Gross et al.

(10) Patent No.: US 8,143,034 B2
(45) Date of Patent: Mar. 27, 2012

(54) METHOD FOR PREPARING LONG-CHAIN HYDROXYACIDS, DIACIDS AND OLIGOMERS AND POLYMERS THEREOF

(75) Inventors: Richard A. Gross, Plainview, NY (US); Wenhua Lu, Brooklyn, NY (US); Yixin Yang, Brooklyn, NY (US)

(73) Assignee: Polytechnic Institute of New York University, Brooklyn, NY (US)

( * ) Notice: Subject to any disclaimer, the term of this patent is extended or adjusted under 35 U.S.C. 154(b) by 749 days.

(21) Appl. No.: 12/195,996

(22) Filed: Aug. 21, 2008

(65) Prior Publication Data

US 2009/0054610 A1   Feb. 26, 2009

Related U.S. Application Data

(60) Provisional application No. 60/957,051, filed on Aug. 21, 2007.

(51) Int. Cl.
  *C12P 7/64* (2006.01)
  *C08F 20/64* (2006.01)
  *C07C 57/02* (2006.01)
(52) U.S. Cl. ............ 435/134; 526/318.3; 554/223
(58) Field of Classification Search ............ 435/134; 526/318.3; 554/223
  See application file for complete search history.

(56) References Cited

U.S. PATENT DOCUMENTS

| | | | | |
|---|---|---|---|---|
| 4,339,536 A * | 7/1982 | Kato et al. | ............ | 435/142 |
| 4,474,882 A * | 10/1984 | Kunishige et al. | ............ | 435/142 |
| 5,962,624 A * | 10/1999 | Vonderhagen et al. | ........ | 528/274 |
| 6,004,784 A * | 12/1999 | Mobley et al. | ............ | 435/134 |
| 7,405,063 B2 * | 7/2008 | Eirich et al. | ............ | 435/123 |
| 2004/0161464 A1 * | 8/2004 | Domb | ............ | 424/486 |

* cited by examiner

*Primary Examiner* — Herbert J Lilling
(74) *Attorney, Agent, or Firm* — Laurence P. Colton; Smith Risley Tempel Santos LLC

(57) ABSTRACT

A method and process for the preparation of ricinoleic acid analogs and oligomers and polymers containing such ricinoleic acid analogs.

38 Claims, 1 Drawing Sheet

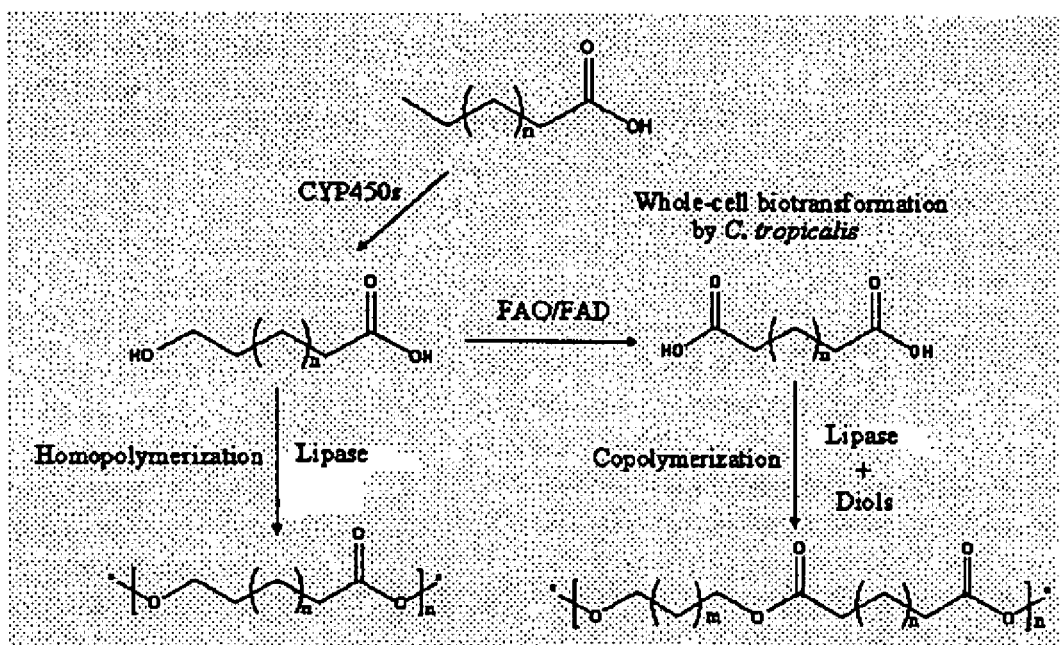

METHOD FOR PREPARING LONG-CHAIN HYDROXYACIDS, DIACIDS AND OLIGOMERS AND POLYMERS THEREOF

STATEMENT OF RELATED APPLICATIONS

This application is based on and claims the benefit of U.S. Provisional Patent Application No. 60/957,051 having a filing date of 21 Aug. 2007.

BACKGROUND OF THE INVENTION

1. Technical Field

This invention relates to methods for preparing long chain α,ω-hydroxyacids and diacids and to oligomers and polymers comprising such compounds.

2. Prior Art

Microorganisms and their enzymes have long been utilized as biocatalysts in the preparation of various products. In recent years, there has been a growing interest in the use of microorganisms and their enzymes in commercial activities not normally recognized as being amenable to enzyme use.

Aliphatic polyesters are a group of biodegradable polymers that may be synthesized from readily renewable building blocks such as lactic acid- and fatty acid-derived materials. Aliphatic polyesters can be synthesized via polycondensation reactions between aliphatic dicarboxylic acids with diols, transesterification of diesters with diols, polymerization of hydroxy acids, and ring-opening polymerization of lactones. Resulting products can be used in industrial and biomedical applications such as for controlled release drug carriers, implants and surgical sutures. Moreover, polyesters with functional groups along chains or in pendant groups are attracting increased interest since these groups can be used to regulate polymeric material properties. Furthermore, functional polymers can be post-modified by attaching different biologically active groups that allow the preparation of biomaterials for use in drug delivery system and as scaffold materials for tissue engineering.

Both chemical and enzymatic approaches have been explored to synthesize functional polyesters. Chemical synthetic methods often require harsh reaction conditions and metal catalysts that are difficult to remove subsequent to polymerizations. Introduction of functional groups along chains or in pendant groups is difficult by chemical methods due to the lack of selectivity of chemical catalysts and associated harsh reaction conditions.

Polyesters, oligomers and polymers from ricinoleic acid have proven highly valuable for many applications, including controlled drug delivery systems. However, high purity ricinoleic acid can be expensive due to difficulties in its purification from the natural mixture. Currently, less costly α,ω-dicarboxylic acids are almost exclusively produced by chemical conversion processes. The chemical processes for production of α,ω-dicarboxylic acids from non-renewable petrochemical feedstocks usually produce numerous unwanted byproducts, require extensive purification, and give low yields (Bio/Technology 10: 894-898 (1992)). While several chemical routes to synthesize long-chain α,ω-dicarboxylic acids are available, their synthesis can be difficult, costly and requires toxic reagents.

Accordingly, there is a need for a process or method for producing ricinoleic acid analogs, which can have internal functionality that may consist of double bonds, triple bonds, epoxide, secondary hydroxyl, Si—O—Si and other moieties, in which the functional groups are transferred into the resulting dicarboxylic acids.

BRIEF SUMMARY OF THE INVENTION

Briefly, this invention includes a process for the preparation of ricinoleic acid analogs by fermentation utilizing microorganisms. Many of these analogs can be subsequently purified and converted into oligomers and polymers for a variety of applications. This invention includes biosynthetic routes that convert compounds such as fatty acids to their corresponding α,ω-dicarboxylic acids, α-carboxyl-ω-hydroxyl fatty acids, ω-, ω-1-dihydroxyl fatty acids or a mixture of these products. For example, it is possible to culture fatty acid substrates with a yeast belonging to *Candida tropicalis*. The yeast converts fatty acids to long-chain ω-hydroxy fatty acids and α,ω-dicarboxylic acids, and mixtures thereof. The yeast also converts terminal mono-alkenes to dihydroxyl fatty acids where the hydroxyl groups are ω- and ω-1-positions of fatty acids. Fermentations can be conducted in liquid media containing fatty acids as substrates.

Biological conversion methods to these compounds can use renewable resources such as fatty acids as starting materials and can provide ricinoleic acid analogs with selectivity and fewer by-products. For example, ω-hydroxy fatty acids and α,ω-dicarboxylic acids can be produced from inexpensive long-chain fatty acids, which are readily available from renewable agricultural and forest products such as soybean oil, corn oil and tallow. Moreover, a wide range of α,ω-dicarboxylic acids with different carbon length (C12-C22) can be prepared because the biocatalyst accepts a wide range of fatty acid substrates.

Additional aspects of specific embodiments include new classes of compounds, including ricinoleic analogs prepared by conversion of mono terminal alkenes with different carbon chain lengths (C12-C18). The resulting ricinoleic analogs are ω-, ω-1 dihydroxy fatty acids with variable chain length. Alkenes used in biological conversions can be derived from renewable resources or petroleum based compounds. In another embodiment, methyl groups of cardanol having different contents of alkene moieties can be converted to carboxylic acids giving new carboxyl cardanol derivatives. The method developed includes partially hydrogenating double bonds of cardanol.

An additional aspect of specific embodiments includes new classes of compounds, which include ricinoleic acid analogs, and new methods for producing these new classes of compounds. The methods involve a biocatalytic step in which fatty acids are transformed to their ω-hydroxy, ω-carboxy, or a mixture of both ω-hydroxy and ω-carboxy ricinoleic analogs. Similar to ricinoleic acid, the analogs prepared can have two functionalities that can be converted via reactions with carboxylic acids or hydroxyl bearing molecules to ester moieties. Ricinoleic analogs also can have an internal functionality that may consist of a double bond, triple bond, epoxide, Si—O—Si and other moieties. Whereas ricinoleic acid has 12-hydroxyl and α-carboxyl groups, ricinoleic analogs described herein have either α-/ω-carboxyl groups, α-carboxyl/ω-hydroxyl groups, or consist of a mixture of these products.

Another aspect of the present invention is that the ricinoleic acid analogs may be copolymerized with a wide array of other monomers such as those with silicone segments, polyols such as glycerol and sorbitol, polyethylene glycol, segments bearing anhydride or carbonate linkages and much more. In one embodiment, the compounds can be converted into aliphatic functional polyesters. These polyesters can be biodegradable, which means they can be converted through biological processes into carbon dioxide, methane, water, lignocellulosic substances and other natural products. In some examples, the polyesters also can function as bioresorbable materials for medical applications. The resulting copolyesters can have variable contents of alkyne, alkene, epoxides and hydroxyl functionalities.

BRIEF DESCRIPTIVE OF THE FIGURES

FIG. 1 shows one scheme of this invention.

DETAILED DESCRIPTION OF THE PREFERRED EMBODIMENTS

Embodiments of this invention provide for methods to synthesize ricinoleic acid analogs using microorganisms. Synthesis of these ricinoleic acid analogs can be accomplished using a whole-cell biocatalyst for conversions of readily fatty acid substrates. One embodiment of this invention provides a process for producing a series of new functional long-chain ω-hydroxy fatty acids, α,ω-dicarboxylic acids, or mixtures of these two products.

1. Recinoleic Acid Analogs

One embodiment of this invention is a method for producing ricinoleic acid analogs using microorganisms in a fermentation process having a seed culture stage and a growth fermentation stage. This method comprises:

a) cultivating a microorganism biomass in a seed culture stage to produce an inoculum;

b) transferring the inoculum into a fermentation medium; and c) maintaining growth stage conditions in the main fermentation stage to facilitate the catalysis of various fatty acids, terminal alkenes, partially hydrogenated cardanol or alkynes to ricinoleic analogs.

Examples of ricinoleic analogs formed via this embodiment include 1,18-cis-9-octadecenedioic acid, 1,22-cis-9-docosenedioic acid, 1,18-cis-9,12-octadecadienedioic acid, 7-hydroxy-cis-9-octadecenedioic acid; 7-hydroxy-1,18-cis-9-octadecenedioic acid, 12,18-dihydroxy-cis-9-octadecenoic acid, cis-9,10-epoxy-1,18-octadecanedioic acid, 7-tetradecynedioic acid, and 8-hexadecynedioic acid. Typical productivity values of these products, using a standard fermentation process, is about 0.1~0.5 g/l/h, and product concentrations were from 10~30 g/l.

Functional substrates suitable with this embodiment include ω-hydroxy fatty acids and α,ω-dicarboxylic acids with carbon chain lengths from C14 to C22 that contain one or more additional functional groups along fatty acid chains that can be selected from the following: alkenes, alkynes, conjugated alkenes, conjugated alkynes, ether, silicone, epoxy, quaternary ammonium salt, secondary amine, imine, and other moieties including —S— and —P(X)—.

As shown in FIG. 1, the products of this invention may be used without further processing or as monomers for oligomer and polymer synthesis. Polymerizations of these monomers may be carried out by chemical or enzymatic methods. As discussed herein, ricinoleic acid building blocks can be further modified or converted to oligomers or polymers via enzymatic polymerizations using a lipase catalyst. This results in a new family of oligomers and polymers with functional groups for post-modification.

A variety of microorganisms can be cultivated for use according to the present invention. Generally, any microorganisms capable of producing enzymes having useful activity, as described herein, can be used in the invention. In specific embodiments, the microorganisms useful according to the invention comprise microorganisms capable of producing acyl-coenzyme A oxidase. A number of acyl-coenzyme A oxidase producing microorganisms are known in the art. *Candida tropicalis, Candida cloacae, Cryptococcus neoforman* and *Corynebacterium* sp. can be used as the whole-cell biocatalyst. *Candida tropicalis* ATCC20962 in which the β-oxidation pathway is blocked by disrupting POX 4 and POX 5 genes encoding acyl-coenzyme A oxidase can be used. For example, *Candida tropicalis* ATCC20962 can be used as catalyst under aerobic conditions in liquid medium to produce ω-hydroxy fatty acids and α,ω-dicarboxylic acids.

The fatty acids or alkynes used have 14 to 22 carbon atoms, can be natural materials obtained from plants, or synthesized from natural fatty acids, such as oleic acid (C18:1), linoleic acid (C18:2), ricinoleic acid (C18:1), erucic acid (C22:1), epoxy stearic acid, 7-tetradecyne and 8-hexadecyne. Naturally derived fatty acids, chemically or enzymatically modified fatty acids, n-alkane, n-alkene, n-alkyne and fatty alcohol that carbon chain length from 12 to 22 are used as carbon sources for the yeast-catalyzed biotransformation. *Candida tropicalis* ATCC20962 is initially cultivated in liquid medium containing inorganic salts, nitrogen source and carbon source. The carbon source for initial cultivations can be saccharide such as sucrose, glucose, sorbitol, etc., and other carbohydrates such as glycerol, acetate, and ethanol. The substrate such as naturally derived fatty acids, chemically or enzymatically modified fatty acids, n-alkane, n-alkene, n-alkyne and fatty alcohol for oxidation of terminal methyl or hydroxyl moieties can be added into the culture.

A versatile and controllable fermentation procedure can be obtained, which, depending on the life cycle, is able to provide well-conditioned constant surroundings for the microorganism. For illustration, the fermentation process can be divided into two phases, which include a growth phase and a transformation phase in which ω-oxidation of the substrate is performed.

The seed culture can be inoculated into the sterile medium with elongated cultivation time at the increasing phase of the pH after its minimum value. In the main fermentation stage, a "steady state" condition with the maximal active ingredient production rate can be maintained for a long time by, inter alia, feeding of the carbon and nitrogen sources in order to supply the nutrient demand; controlling the glucose concentration to avoid the undesirable thickening of the culture and the exaggerated increase in biomass; controlling the stirring rate and aeration rate according to the oxygen demand combining foam level control with the carbon source demand an appropriate material for both purposes, e.g., a mixture of a vegetable oil and a synthetic agent; maintaining the pH between the range of from about 5.2-6.2 with the feeding of carbon source, e.g., glucose syrup, or base; and, carrying out one or more withdrawals, when the maximal working volume of the fermenter is achieved, or when a mevinolin concentration economical enough to carry out the downstream processing is reached.

In one embodiment, a fermentation procedure includes in a culture at a pH between 5.0 and 8.0, at a temperature between about 22° C. and about 30° C. For example, the seeds inoculated from fresh agar plate or glycerol stock can be cultivated in a pre-culture medium for 16-20 h, at 30° C. and about pH 6.5 in a shaker. Subsequently, this culture is used to inoculate the conversion medium with co-substrates. Further, the growth phase of the culture can be performed for about 10-12 h to generate high cell density cultures at about pH 6.5 and about 30° C. The transformation phase is begun with addition of the fatty acid or other substrate for the bio-oxidation.

The medium pH can be adjusted to 7.5-8.0 by addition of a base solution. Co-substrates can be fed during the transformation phase to provide energy for cell growth. By using this method, terminal methyl groups of the fatty acid, synthetically derived substrates, n-alkane, n-alkene, n-alkyne, and fatty alcohol that have carbon chain lengths from 12 to 22 are converted to hydroxyl or carboxyl groups.

The ω-hydroxy fatty acids and α,ω-dicarboxylic acids in fermentation broth can be extracted and purified as follows. The liquid culture medium containing these products is acidified with concentrated hydrochloric acid to pH about 1.0~4.0 and extracted into diethyl ether. Solvent in ether extract is evaporated under vacuum with a rotary evaporator. Resulting product mixtures can be further purified by silica gel column chromatography using silica gel. Chromatographic separations were generally conducted using an eluent that consists of a two-solvent system. Solvents pairs were selected so that one is of low polarity (e.g., n-hexane) while the other is of higher polarity (e.g., diethyl ether).

Fractions containing impurities and products can be eluted separately by adjusting the ratio of strong-to-weak solvent. Alternatively, products mixture can be purified by liquid chromatography methods with various column types including those that are reverse-phase. Chromatographic separations can be conducted using a mixed solvent that consists of various contents of methanol, water, formic acid, and acetonitrile. Fractions containing impurities and products are eluted separately depending on their polarity. Further, ricinoleic acid analogs that have two carboxylic acids or have sufficient polarity to dissolve in alkaline medium can be extracted and precipitated from fermentation broths by a method such as the following.

An alkaline material such as sodium hydroxide or potassium hydroxide is added to the fermentation broth and the pH of the solution is adjusted to 11~13 to dissolve dicarboxylic acids formed. Then, diatomaceous earth in an amount of 2-8% by weight is added to the fermentation broth to selectively absorb lower polarity components of the mixture such as unreacted hydrocarbons and monocarboxylic acids. Subsequently, the fermentation broth is filtered under pressure by using a filter press and the cake formed after this filtration is washed with 2 to 3 times with water. The obtained filtrate is then acidified to a pH of 4.0 or below by addition of an acid such as sulfuric acid or hydrochloric acid to precipitate dicarboxylic acid products. The precipitated dicarboxylic acids can then be further purified by recrystallization using an organic solvent. Generally such an organic solvent would be of low polarity (e.g., n-hexane).

Purified ω-hydroxy fatty acids and α,ω-dicarboxylic acids can be identified by analysis. A sample was esterified with $BF_3$ in methanol (10%, w/w) at 70° C. for 20 min followed by silylation of methyl esters with HMDS/TMCS/Pyridine at 70° C. for 10 min. Analysis of derivatized products was performed by gas chromatography/mass spectrometry (GC/MS). Structures of products were also confirmed by $^1$H- and $^{13}$C-NMR. Quantification of product formation during biotransformations was performed by liquid chromatography/mass spectrometry (LC/MS) using purified products as standards.

2. Oligomers or Polymer of Ricinoleic Acid Analogs

The combination of a method in which ricinoleic acid analogs are synthesized by an oxidative biotransformation and subsequently undergo a catalyzed homo- or copolymerization using an enzyme that in nature functions for ester hydrolysis. While numerous enzymes and catalytic methods can be used to polymerize the recinoliec acid analogs, lipase under reverse equilibrium conditions, can illustrate the nature and scheme to prepare such polyesters.

By first synthesizing a family of novel ricinoleic acid analogs by a yeast-catalyzed biotransformation and then using these products as monomers for polymerizations, a novel family of functional polyesters was prepared. Polymerizations can be performed using an immobilized enzyme catalyst, such as immobilized *Candida antartica* Lipase B (CALB). Novozym 435 is an example of an immobilized CALB where the immobilization support consists of macroporous polymethylmethacrylate beads. Cutinases and esterases also are suitable.

Polymerization of the ricinoleic acid analog monomers also can be carried out chemically by using chemical catalysts instead of a lipase, esterase, or cutinase. Chemical catalysts suitable include those catalysts used to catalyze condensation polymerizations including, but not limited to, tin octanoate and titanium alkoxides.

Enzyme-catalyzed homo- and copolymerizations allow control of branching when using monomers with 3 or more reactive groups. Furthermore, enzyme-catalysis allows the synthesis of carbonate, ester, amide, and anhydride linkages between monomers. Moreover, mild conditions during enzyme-catalysis allows functional groups along monomers such as alkynes, alkenes, conjugated alkynes, conjugated alkenes, epoxides, hydroxyl, silicone, and more to remain intact during polymer synthesis. In another embodiment, the synthesis of random aliphatic poly(carbonate-co-esters) could be derived from conventional monomer feeds. For example, equal molar ratios of diacids and diols can be used with 10%-by-wt Novozym 435. For homopolymerizations of ω-hydroxy fatty acids, only ω-hydroxy fatty acid is added. Although copolymerizations of ω-hydroxy fatty acid monomers can also be performed with other hydroxyl fatty acids and/or with diacids and diols, specific embodiment can have better results by retaining equimolar stoichiometry of reactive acid and hydroxyl groups.

To drive the reaction to completion, it may be necessary to remove water and/or the alcohol (e.g., ethanol when using diethylcarbonate) that is evolved during the condensation reaction. Water and/or ethanol can be removed from the reaction through numerous techniques, e.g., a vacuum, well established in the art. For example, the water/ethanol byproduct of condensation reactions can be removed by reducing the pressure or applying a vacuum. Alternatively, water and/or ethanol can be removed with a wiped film evaporator under reduced pressure. In another alternative method a desiccant such as a molecular sieve is used, taking precautions to avoid physical damage to supported enzymes due to abrasion between the desiccant and the enzyme support. Another alternative can include passing dry air or nitrogen into the reaction mixture so that water and/or ethanol is transferred from the reaction mixture to the air that subsequently leaves the reaction vessel.

The reaction in this method can be quenched by means understood by persons of ordinary skill in the art. For example, the reactions can be terminated by addition of cooled chloroform and removal of the enzyme-catalyst by filtration. Alternatively, the products can be separated from the catalyst by filtration without addition of solvents as long as the product has sufficiently low viscosity. Also, the catalyst can be deactivated by another method such as denaturation by heating the product. Catalyst can also be left within the product after the catalyst is deactivated. If product fractionation is desired to increase molecular weight or to separate components of the product, then precipitation can be performed.

Preferably the product is used without fractionation. To precipitate polymeric products the resulting chloroform solution was slowly added with stirring to methanol.

Polymerizations can be performed in a parallel synthesizer under various conditions. For example, the polymerization can be performed in bulk, in diphenyl ether, or in toluene. For solution polymerizations, minimal volumes of diphenyl ether or toluene can be added to decrease diffusion constraints that would otherwise limit molecular weights formed and the rate at which polymerizations occur.

Properties of resulting polyesters were analyzed by the following methods. The molecular weight averages and polydispersity of functional polyesters were determined by gel permeation chromatography (GPC). Structures were analyzed by $^1$H-NMR and $^{13}$C-NMR. The thermal properties were determined by thermogravimetric analysis (TGA) and differential scanning calorimetry (DSC). Polymers with $M_w$ values ranging from about 20 000 to 80 000 with polydispersities ($M_w/M_n$) of between about 2.0 and 3.1 were prepared.

As the analogs produced by this invention were novel analogs, the functional polyesters were synthesized as examples were also new. Functional groups of ricinoleic acid analogs such as alkene, alkyne, and epoxide moieties could be maintained intact during enzyme-catalyzed polymer synthesis. Examples of novel functional polyesters prepared include polymers with repeat units containing double bonds, triple bonds, hydroxyl, and epoxide moieties. This was accomplished by homopolymerization of 12,18-dihydroxy-cis-9-octadecenoic acid as well as by copolymerization of α,ω-dicarboxylic acids that include 1,18-cis-9-octadecenedioic acid, 1,22-cis-9-docosenedioic acid, 7-hydroxy-1,18-cis-9-octadecenedioic acid, cis-9,10-epoxy-1,18-octadecanedioic acid, and 7-tetradecynedioic acid with diols such as 1,8-octanediol, 1,3-propanediol and glycerol.

The present invention is now further illustrated in detail by the following examples.

Example 1

Exemplary Biotransformation Procedure

C. tropicalis ATCC20962 from fresh agar plate or glycerol stock was precultured in 30 ml YPD medium consisting of (g/l): yeast extract, 10; peptone, 10; glucose, 20 and shaken at 250 rpm, 30° C. for 20 h in 500 ml flask. After 16 h of cultivation at 250 rpm, 30° C., preculture was inoculated at 10% (v/v) to 30 ml conversion medium consisting of (g/l): peptone, 30° C.; yeast extract, 6; yeast nitrogen base, 6.7; acetic acid, 3; $K_2HPO_4$, 7.2; $KH_2PO_4$ 9.3; glucose/glycerol, 20° C., in 500 ml flask and shaked at 250 rpm. The initial concentration of substrate was about 10-20 g/l. The pH was adjusted to 7.5 by addition of 2 mol/l NaOH solution after 12 h. During the biotransformation, concentrated co-substrate (glucose/glycerol/sodium acetate/ethanol) was fed (1-2.5% per day) and the pH was maintained at 7.5~8.0 by adding NaOH solution. Samples were taken on a daily basis to determine levels of product by LC-MS.

Example 2

Exemplary Biotransformation Procedure in Fermentor

Fermentation was carried out in 3-l Bioflo3000 fermentor (New Brunswick Scientific Co., USA) in fed-batch culture. The conversion medium mentioned above in Example 1 was used but modified by adding 0.05% antifoam 204 (Sigma) and 0.5% substrate. The seed culture from fresh agar plate or glycerol stock was prepared in 50 ml of conversion medium for 20 h at 30° C., 250 rpm prior to inoculation into the fermentor vessel. Following inoculation, the culture was maintained at pH of 6.3 and grown at 30° C., 900 rpm with aeration rate of 1.5 vvm. After 12 h fermentations (growth phase), biotransformation phase was started with feeding of substrate (2 ml/l). Concentrated glucose (500 g/l) as co-substrate was fed continuously at the rate of 1.2 g/l/h. During the biotransformation phase, pH was maintained at 7.6 automatically by addition of 4 mol/l NaOH solution. Antifoam (Antifoam 204) was also added to the fermentor as necessary. Samples were taken on a daily basis to determine levels of product by LC-MS.

Example 3

Exemplary Extraction and Purification Procedure of Biotransformation Products The fermentation broth was acidified to pH of 1.0 with HCl and extracted twice with diethyl ether. To avoid an epoxy ring-opening during acidification, the fermentation broth with products containing epoxy groups was slowly acidified to pH 3.0 with 5 N HCl. Solvent was evaporated under vacuum with a rotary evaporator. The residual obtained was separated by silica gel column chromatography using silica gel 60. The fractions containing impurities, un-reacted mono fatty acids and products were gradually eluted with a mixture of n-hexane/diethyl ether that their ratio ranges from 90:30 to 10:90. The fractions containing same compound were collected together and the solvents were evaporated under vacuum with a rotary evaporator.

Example 4

Synthesis of cis-9,10-epoxy-1,18-octadecanoic Acid by Lipase-Mediated Epoxidation of Oleic Acid Cis-9,10-epoxy-1,18-octadecanoic acid was synthesized from oleic acid by the chemo-enzymatic method. The reaction was performed in 50-ml bottom flask containing 0.5 M oleic acid in 20 ml toluene and 300 mg immobilized CALB (Novozym 435). Hydrogen peroxide (30%, w/w) was added stepwise at the rate of 0.5 ml every one hour during the first 4 h. The reaction mixtures were stirred at 600 rpm and reaction temperature was maintained at 50° C. After 8 h reaction, the reaction was terminated and Novozym 435 was removed from solvent by filter. Cis-9,10-epoxy-1,18-octadecanoic acid was obtained by removing toluene under vacuum with a rotary evaporator.

Example 5

Exemplary Procedure for Polymer Synthesis Catalyzed by Novozym 435

Reaction was carried out in a parallel synthesizer (Advantage™ 2050, Argonaut) in bulk or in diphenyl ether. Purified functional diacids (1.0 mmol) and 1,8-octanediol or 1,3-propanediol (1.0 mmol) were transferred into reactor tubes in the parallel synthesizer and 10%-by-weight Novozym 435 was added. For homopolymerizaiton, only ω-hydroxy fatty acid (2.0 mmol) was added. A vacuum (2.0 psi) was applied after 2 h. To follow the progress of polymerizations aliquots were withdrawn at 2, 6, 12, 24, 36 and 48 h. Reactions were terminated by addition of cooled chloroform and Novozym 435 was removed by filtration. The filtrates were directly analyzed by gel permeation chromatography (GPC) to determine molecular weight averages and polydispersity.

The final product mixtures were directly analyzed by $^1$H-NMR. The reaction was also carried out in toluene in 250 ml round bottom flask. The purified functional diacids (20 mmol) and 1,8-octanediol or 1,3-propanediol (20 mmol) were transferred into flask with 100 ml toluene and 10%-by-weight Novozym 435 was added. Vacuum (2.0 psi) was applied after 2 h. Reactions were terminated by addition of cooled chloroform and Novozym 435 was removed by filtration. The filtrates were directly analyzed by gel permeation chromatography (GPC) to determine molecular weight averages and polydispersity. The product mixture at the final time point was dissolved in chloroform and then filtered to remove the catalyst. The resulting chloroform solution was slowly added with stirring to methanol to precipitate polymeric product. The precipitated polymer was washed with methanol three times and then dried using vacuum evaporator at 50° C. for the analysis of $^1$H-NMR and thermal properties.

Example 6

Production of 1,18-cis-9-octadecenedioic Acid from Oleic Acid by Biotransformation with *C. tropicalis* ATCC20962 in Shake-Flask Experiment The biotransformation of oleic acid was carried out in 500 ml flask according to the culture condition described in Example 1. Glucose was used as co-substrate and initial concentration was 20 g/l. After the culture was grown for 12 h, 20 g/l of oleic acid was added into the culture and pH was adjusted to about 7.5. After 48 h, oleic acid was largely transformed to the corresponding 1,18-cis-9-octadecenedioic acid which reached 18 g/l. The productivity of the unsaturated diacid was about 0.38 g/l/h. The double bond appeared to remain during the biotransformation.

Example 7

Production of 1,18-cis-9-octadecenedioic Acid from Oleic Acid by Biotransformation with *C. tropicalis* ATCC20962 in Fermentor Fermentation was carried out in a 3 l fermentor according to the fermentation condition described in Example 2. The culture was grown at 30° C., and at a pH of 6.3 with aeration at a rate of 2 l/min for 12 hours. Conversion was initiated by feeding of oleic acid at the rate of 2 ml/h. The pH of the culture was maintained at 7.6 with automatically addition of 4 mol/l NaOH. Glucose solution was fed at the rate of 1.2 g/l/h. After a 60 h biotransformation, the concentration of 1,18-cis-9-octadecenedioic acid reached to 31 g/l with the productivity of 0.52 g/l/h. The double bond appeared to remain during biotransformation.

Example 8

Production of 1,22-cis-9-docosenedioic Acid from Erucic Acid by Biotransformation with *C. tropicalis* ATCC20962

The biotransformation of erucic acid was carried out in 500 ml flask according to the culture condition described in Example 1. Glucose or glycerol was used as co-substrate and initial concentration was 20 g/l. After 12 h culture growth, 20 g/l of erucic acid was added into the culture and pH was adjusted to about 7.5. After a 72 h biotransformation, the concentration of 1,22-cis-9-docosenedioic acid reached to 15 g/l with the productivity of 0.21 g/l/h. The double bond remain during biotransformation.

Example 9

Production of 1,18-cis-9,12-octadecadienedioic Acid from Linoleic acid by Biotransformation with *C. tropicalis* ATCC20962

The biotransformation of linoleic acid was carried out according to the procedure described in Example 1. Glucose was used as co-substrate at an initial concentration was 20 g/l. After 12 h, 20 g/l of linoleic acid was added into the culture and the pH was adjusted to about 7.5. After a 24 h biotransformation, the concentration of 1,18-cis-9,12-octadecadienedioic acid reached to 7 g/l. Thereafter, an increase in the fermentation time resulted in decreased diacid concentration. The double bonds remained during biotransformation.

Example 10

Production of 12,18-dihydroxy-cis-9-octadecenoic Acid and 7-hydroxy-1,18-cis-9-octadecenedioic Acid from Ricinoleic Acid by Biotransformation with *C. tropicalis* ATCC20962 in Shaker-Flask Experiment Biotransformation of ricinoleic acid was carried out according to the culture condition described in Example 1. Mixtures of 12,18-dihydroxy-cis-9-octadecenoic acid and 7-hydroxy-1,18-cis-9-octadecenedioic acid were obtained with retention of the secondary hydroxyl group at the 12-position. The ratio of 12,18-dihydroxy-cis-9-octadecenoic acid to 7-hydroxy-1,18-cis-9-octadecenedioic acid was significantly affected by the culture conditions. The conversion rate of ricinoleic acid was greater with increased aeration of cultures that was achieved by using higher shake-flask agitation rates. Cultures performed with relatively higher agitation (250 rpm) rapidly convert 12,18-dihydroxy-cis-9-octadecenoic acid that accumulates in flasks to 7-hydroxy-1,18-cis-9-octadecenedioic acid. After 72 h, the concentration of 7-hydroxy-1,18-cis-9-octadecenedioic acid reached to 9 g/l. By decreasing the agitation rate in flasks, the ratio of ω-hydroxy to diacid increased. At 150 rpm shaker speed, the molar ratio of these products is 1:1 with a total conversion from ricinoleic acid of 75 mol %. By using glycerol as co-substrate, >90% conversion of ricinoleic acid to 7-hydroxy-1,18-cis-9-octadecenedioic acid was achieved.

In contrast, using ethanol as a co-substrate resulted in lower conversion of ricinoleic acid but the major product formed was 12,18-dihydroxy-cis-9-octadecenoic acid that reached to about 5 g/l. The ratio of ω-hydroxy to diacid was also increased by increasing the initial concentration of ricinoleic acid in culture medium.

Example 11

Production of 12,18-dihydroxy-cis-9-octadecenoic Acid and 7-hydroxy-1,18-cis-9-octadecenedioic Acid from Ricinoleic Acid by Biotransformation with *C. tropicalis* ATCC20962 in Fermentor Fermentation was carried out in a 3 l fermentor according to Example 2. The culture was grown for 12 h at 30° C. and at a pH of 6.3. The dissolved oxygen was controlled at 30% and 60%, respectively. At high DO (60%), all ricinoleic acid was converted to 7-hydroxy-1,18-cis-9-octadecenedioic acid and the concentration was about 12 g/l after 72 h conversion. A mixture of 12,18-dihydroxy-cis-9-octadecenoic acid (4.7 g/l) and 7-hydroxy-1,18-cis-9-octadecenedioic acid (4.9 g/l) was obtained at lower DO (30%). The secondary hydroxyl group remained during biotransformation.

Example 12

Production of cis-9,10-epoxy-1,18-octadecanedioic Acid from cis-9,10-epoxy-1,18-octadecanoic Acid by Biotransformation with *C. tropicalis* ATCC20962 in Shaker-Flask Experiment Cis-9,10-epoxy-1,18-octadecanoic acid were synthesized from oleic acid using chemo-enzymatic method according to the procedure described in Example 4. Biotransformation of cis-9,10-epoxy-1,18-octadecanoic acid was carried out in 500 ml flask according to the culture condition described in Example 1. Glucose was used as co-substrate and initial concentration was 20 g/l. After 12 h culture, 20 g/l of cis-9,10-epoxy-1,18-octadecanoic acid was added into the culture and pH was adjusted to about 7.5. After a 72 h biotransformation, the concentration of cis-9,10-epoxy-1,18-octadecanedioic acid reached to 19.1 g/l with the productivity of 0.27 g/l/h. The epoxy group remained during biotransformation.

Example 13

Production of 7-tetradecynedioic Acid from 7-tetradecyne by Biotransformation with *C. tropicalis* ATCC20962 in Shaker-Flask Experiment Biotransformation of 7-tetradecyne was carried as described in Example 1. Glucose was used as co-substrate and initial concentration was 20 g/l. After 12 h, 20 g/l of 7-tetradecyne was added into the culture and pH was adjusted to about 7.5. After a 96 h biotransformation, the concentration of 7-tetradecynedioic acid reached to 11 g/l with the productivity of 0.12 g/l/h. The triple bond remained during the biotransformation.

Example 14

Production of 8-hexadecynedioic Acid from 8-hexadecyne by Biotransformation with *C. tropicalis* ATCC20962 in Shaker-Flask Experiment Biotransformation of 8-hexadecyne was carried out in 500 ml flask according to the culture condition described in Example 1. Glucose was used as co-substrate and initial concentration was 10 g/l. After 12 h, 20 g/l of 8-hexadecyne was added into the culture and pH was adjusted to about 7.5. After a 96 h biotransformation, the concentration of 8-hexadecynedioic acid reached to 6.5 g/l with the productivity of 0.07 g/l/h. The triple bond remained during biotransformation.

Example 15

Synthesis of Polyesters Containing Double Bonds from 1,18-cis-9-octadecenedioic acid and 1,8-octanediol Catalyzed by Novozym 435

Copolymerization of 1,18-cis-9-octadecenedioic acid ($\omega$-carboxyoleic acid, $\omega$-HOOC—OA) with 1,8-octanediol (OD) was carried out in both diphenyl ether and in bulk catalyzed by N435 as described in Example 5. The reaction temperature was 90° C. The copolymers were successfully synthesized. Molecular weights (Mw) of poly($\omega$-HOOC-OA-co-OD) were 57,000 (PDI=2.02) at 36 h and 44,000 (PDI=2.61) at 48 h in diphenyl ether and in bulk, respectively. $^1$H-NMR results showed double bonds were untouched during polymerization.

Copolymerization of 1,18-cis-9-octadecenedioic acid ($\omega$-carboxyoleic acid, $\omega$-HOOC-OA) with 1,8-octanediol (OD) was also carried out in toluene in round bottom flask catalyzed by N435 described in Example 5. The reaction temperature was 90° C. Molecular weight (Mw) and PDI of poly($\omega$-HOOC-OA-co-OD) were 94,000 and 2.05, respectively.

Example 16

Synthesis of Polyesters Containing Double Bonds from 1,18-cis-9-octadecenedioic Acid and 1,3-propanediol Catalyzed by Novozym 435

Copolymerization of 1,18-cis-9-octadecenedioic acid ($\omega$-carboxyoleic acid, $\omega$-HOOC-OA) with 1,3-propanediol (PD) was carried out in both diphenyl ether and in bulk catalyzed by N435 described in Example 5. The reaction temperature was 90° C. The copolymers were successfully synthesized. Molecular weights (Mw) of poly($\omega$-HOOC-OA-co-PD) were 53,000 (PDI=2.32) at 36 h and 26,000 (PDI=1.75) at 48 h in diphenyl ether and in bulk, respectively. $^1$H-NMR results showed double bonds were during polymerization.

Example 17

Synthesis of Polyesters Containing Double Bonds from 1,18-cis-9-octadecenedioic Acid and Glycerol Catalyzed by Novozym 435

Copolymerization of 1,18-cis-9-octadecenedioic acid ($\omega$-carboxyoleic acid, $\omega$-HOOC-OA) with glycerol (GL) was carried out in diphenyl ether described in Example 5. After 36 h reaction, molecular weight (Mw) of the copolymer, poly($\omega$-HOOC-OA-co-GL) reached to 29,000 with PDI of 2.17. Double bonds remained untouched during polymerization.

Example 18

Synthesis of Polyesters Containing Double Bonds from 1,22-cis-9-docosenedioic Acid and 1,8-octanediol Copolymerization of 1,22-cis-9-docosenedioic acid ($\omega$-carboxyerucic acid, $\omega$-HOOC-EA) with 1,8-octanediol (OD) was carried out in both diphenyl ether and in bulk catalyzed by Novozym 435 described in Example 5. The reaction temperature was 90° C. The copolymers were successfully synthesized. Molecular weights (Mw) of poly($\omega$-HOOC-EA-co-OD) were 32,000 (PDI=1.95) and 29,000 (PDI=2.14) after 36 h in diphenyl ether and in bulk, respectively. The double bonds were maintained during polymerization.

Example 19

Synthesis of Polyesters Containing Double Bonds and Hydroxyl Groups from 7-hydroxy-cis-9-octadecenedioic Acid and 1,8-octanediol Catalyzed by Novozym 435

Copolymerization of 7-hydroxy-cis-9-octadecenedioic acid ($\omega$-carboxyricinoleic acid, $\omega$-HOOC-RA) and 1,8-octanediol was catalyzed by N435 described in Example 5.

Copolymer molecular weights for polymerizations in diphenyl ether and in-bulk were 40,000 and 28,000 with PDI (Mw/Mn) of 2.00 and 2.22, respectively. $^{13}$C-NMR analysis of copolymers showed about 7% of polymerization was happed in secondary hydroxyl groups.

Example 20

Synthesis of Polyesters Containing Double Bonds and Hydroxyl Groups from 12,18-dihydroxy-cis-9-octadecenoic Acid Catalyzed by Novozym 435

Homopolymerization of 12,18-dihydroxy-cis-9-octadecenoic acid (ω-hydroxy ricinoleic acid, ω-HO-RA) was catalyzed by N435 in diphenyl ether described in Example 5. The molecular weight increased gradually throughout the 48 h reaction and reached Mw 67,000 and PDI (Mw/Mn) of 2.30. $^{13}$C-NMR analysis of the polymer showed that the polymerization was both in primary hydroxyl group (864%) and in secondary hydroxyl group (14%).

Example 21

Synthesis of Polyesters Containing Epoxy Groups from cis-9,10-epoxy-1,18-octadecanedioic Acid and 1,8-octanediol Catalyzed by Novozym 435

N435-catalyzed copolymerization of cis-9,10-epoxy-1,18-octadecanedioic acid with 1,8-octanediol (OD) to prepare epoxy-functionalized polyesters were conducted both in-bulk and in diphenyl ether described in Example 5. The copolymer was successfully synthesized. For N435-catalyzed polymerizations in diphenyl ether, the highest molecular weights (Mw) of poly(ω-HOOC-Epoxy SA-co-OD) were 26,000 with PDI of 2.90. Mw decreased after 36 h reactions. By performing polymerizations in-bulk, poly(ω-HOOC-Epoxy SA-co-OD) was prepared with Mw and PDI values of 39,000 and 3.10, respectively. $^1$H-NMR results showed epoxy group were untouched during the polymerization.

Example 22

Synthesis of Polyesters Containing Epoxy Groups from cis-9,10-epoxy-1,18-octadecanedioic Acid and 1,3-propanediol Catalyzed by Novozym 435

N435-catalyzed copolymerization of cis-9,10-epoxy-1,18-octadecanedioic acid with 1,3-propanediol (PD) to prepare epoxy-functionalized polyesters was conducted in diphenyl ether described in Example 5. The highest molecular weights (Mw) of poly(ω-HOOC-Epoxy SA-co-PD) was 73,000 with PDI of 2.99 after 24 h reaction. $^1$H-NMR results showed epoxy group were maintained during the polymerization.

Example 23

Synthesis of Polyesters Containing Triple Bonds from 7-tetradecynedioic Acid and 1,8-octanediol Catalyzed by Novozym 435

Copolymerization of 7-tetradecynedioic acid and 1,8-octanediol was catalyzed by N435 in diphenyl ether described in Example 5. The molecular weights (Mw) and PDI values of the resulting polyester were 62,000 and 2.15 after 36 h reaction, respectively. $^1$H-NMR results showed the triple bond remained untouched during the polymerization.

Example 24

Synthesis of Polyesters from 1,18-octadecanedioic Acid and 1,8-octanediol

Copolymerization of 1,18-octadecanedioic acid (ω-carboxystearic acid, ω-HOOC-SA) with 1,8-octanediol (OD) was carried out in toluene in round bottom flask catalyzed by Novozym 435 described in Example 5. The reaction temperature was 90° C. After 48 h reaction, the molecular weight and PDI of poly(ω-HOOC-SA-co-OD) were 76,000 and 2.00, respectively. The resulting saturated polyester was used for the comparison of thermal properties to the polyesters with functional groups.

Example 25

Thermal Properties of the Polyesters with Functional Groups

The thermal properties of synthesized polyesters with functional groups were analyzed by thermogravimetric analysis (TGA) and differential scanning calorimetry (DSC). The details are showed in Table 1.

TABLE 1

Thermal properties of polyesters with functional groups

| Polyester | $M_w$ | $M_w/M_n$ | $T_d$ (° C.)[a] | $T_m$ (° C.)[b] |
|---|---|---|---|---|
| Poly(ω-HOOC-OA-co-OD) | 44,000 | 2.61 | 388 | 23/36 |
| Poly(ω-HOOC-EA-co-OD) | 29,000 | 2.14 | 385 | 35/40 |
| Poly(ω-HOOC-RA-co-OD) | 28,000 | 2.22 | 364 | −0.3/21 |
| Poly(ω-HOOC-Epoxy SA-co-OD) | 39,000 | 3.10 | 381 | 33 |
| Poly(ω-HOOC-SA-co-OD) | 76,000 | 2.00 | 360 | 77/88 |

[a]Data from TGA in nitrogen atmosphere at a heating rate of 10° C./min from 25° C. to 700° C.
[b]Data from DSC based on the second heating run at 10° C./min.

Example 26

Production of 13,14-dihydroxytetradecanoic Acid from 1-tetradecene by Biotransformation with C. tropicalis ATCC20962 in Fermentor Fermentation was carried out in a 3 l fermentor according to the fermentation condition described in Example 2. The culture was grown at 30° C., and at a pH of with aeration at a rate of 2 l/min for 12 hours. Conversion was initiated by addition of 20 g/l 1-tetradecene. The pH of the culture was maintained at 7.8 with automatically addition of 4 mol/l NaOH. Glucose solution was fed at the rate of 1.2 g/l/h. After a 80 hour biotransformation, the concentration of 13,14-dihydroxytetradecanoic acid reached to 5.8 g/l with the productivity of 0.07 g/l/h.

Example 27

Production of 15,16-dihydroxyhexadecanoic Acid from 1-hexadecene by Biotransformation with C. tropicalis ATCC20962 in Fermentor Fermentation was carried out in a 3 l fermentor according to the fermentation condition described in Example 2. The culture was grown at 30° C., and at a pH of 6.3 with aeration at a rate of 2 l/min for 12 hours. Conversion was initiated by addition of 20 g/l 1-hexadecene. The pH of the culture was maintained at 7.8 with automatically addition of 4 mol/l NaOH. Glucose solution was fed at the rate of 1.2 g/l/h. After a 60 hour biotransformation, the concentration of 15,16-dihydroxyhexadecanoic acid reached to 6.2 g/l with the productivity of 0.1 g/l/h.

Example 28

Production of 17,18-dihydroxyoctadecanoic Acid from 1-octadecene by Biotransformation with *C. tropicalis* ATCC20962 in Fermentor Fermentation was carried out in a 3 l fermentor according to the fermentation condition described in Example 2. The culture was grown at 30° C., and at a pH of 6.3 with aeration at a rate of 2 l/min for 12 hours. Conversion was initiated by addition of 20 g/l 1-octadecene. The pH of the culture was maintained at 7.8 with automatically addition of 4 mol/l NaOH. Glucose solution was fed at the rate of 1.2 g/l/h. After a 60 hours biotransformation, the concentration of 17,18-dihydroxyoctadecanoic acid reached to 5.4 g/l with the productivity of 0.09 g/l/h.

Example 29

Production of ω-carboxyl Cardanol from Partially Hydrogenated Cardanol by Biotransformation with *C. tropicalis* ATCC20962 in Fermentor Partially hydrogenated cardanol was synthesized from commercial cardanol catalyzed by platinum in activated carbon with existence of hydrogen. Hydrogenation of commercial cardanol after an 8 hour reaction gave ~25% saturated cardanol, ~60% mono-unsaturated cardanol and ~15% di-unsaturated cardanol.

Fermentation was carried out in a 3 l fermentor according to the fermentation condition described in Example 2. The culture was grown at 30° C., and at a pH of 6.3 with aeration at a rate of 2 l/min for 16 hours. Conversion was initiated by addition of 20 g/l partially hydrogenated cardanol. The pH of the culture was maintained at 7.6 with automatically addition of 4 mol/l NaOH. Glucose solution was fed at the rate of 1.8 g/l/h. After a 96 hour biotransformation, the total conversion ratio to ω-carboxyl cardanol reached to 22% with the concentration of 4 g/l.

Fermentation was also carried out in a 3 l fermentor with DO-stat controlled feeding of glucose. The culture was grown at 30° C., and at a pH of 6.3 with aeration at a rate of 2 l/min for 16 hours. Conversion was initiated by addition of 20 g/l partially hydrogenated cardanol. The pH of the culture was maintained at 7.6 with automatically addition of 4 mol/l NaOH. Glucose solution was fed using DO-stat controlled mode. The feeding of glucose was initiated when DO was higher than 55%, and stopped when DO value was lower than 50% during conversion phase. After a 96 hour biotransformation, the total conversion ratio to ω-carboxyl cardanol reached to 40% with the concentration of 7.6 g/l.

NMR results show that the resulting ω-carboxyl cardanol consists of about 15% saturated ω-carboxyl cardanol, about 65% mono-unsaturated ω-carboxyl cardanol and about 20% di-unsaturated ω-carboxyl cardanol.

Example 30

Synthesis of Polyesters Containing Hydroxyl Groups from 13,14-dihydroxytetradecanoic Acid Homo-polymerization of 13,14-dihydroxytetradecanoic acid was carried out in toluene in diphenyl ether catalyzed by Novozym 435 described in Example 5. The reaction temperature was 90° C. After 48 h reaction, the molecular weight and PDI of the resulting polyester were 51,000 and 4.20, respectively.

New functional ω-hydroxy fatty acids and α,ω-dicarboxylic acids can be used as raw materials for the preparation of perfumes, engineered plastics, adhesives, lubricants, and as monomers for the synthesis of polymers that are biodegradable in various disposable environments. Alternatively, the polymers formed can be used as novel bioresorbable medical materials. Functional groups along polymers can be used to bind or chemically link bioactive moities to regulate the biological properties of these materials. Another use of functional polyesters is in industrial coating formulations, components in drug delivery vehicles and scaffolds that support cell growth during tissue engineering and other regenerative medicine strategies.

This detailed description of the preferred embodiments and the appended FIGURE have been presented only for illustrative and descriptive purposes, are not intended to be exhaustive and are not intended to limit the scope and spirit of the invention. The embodiments were selected and described to best explain the principles of the invention and its practical applications, and one skilled in the art will recognize that many variations can be made to the invention disclosed herein without departing from the scope and spirit of the invention.

What is claimed is:
1. A method for producing ricinoleic acid analogs comprising the steps of:
   a) cultivating a microorganism in a seed culture stage to produce an inoculum, wherein the microorganism is selected from the group consisting of microorganisms capable of producing P450 mono-oxygenase;
   b) transferring the inoculum into a fermentation medium; and
   c) maintaining growth stage conditions in a main fermentation stage to facilitate the catalysis of a substrate to ricinoleic acid analogs, wherein the main fermentation stage is maintained at a pH of between about 5.0 and 8.0 and a temperature of between about 22° C. and about 30° C. for a time period of between about 10-12 hours,
   wherein the resulting ricinoleic acid analog has a formula selected from the group consisting of 1,18-cis-9-octadecenedioic acid; 1,22-cis-9-docosenedioic acid; 1,18-cis-9,12-octadecadienedioic acid; 7-hydroxy-1,18-cis-9-octadecenedioic acid; 12,18-dihydroxy-cis-9-octadecenoic acid; cis-9,10-epoxy-1,18-octadecanedioic acid; 7-tetradecynedioic acid; and 8-hexadecynedioic acid.

2. The method as claimed in claim 1, wherein the substrate is a fatty acid.

3. The method as claimed in claim 2, wherein the fatty acid is selected from the group consisting of w-hydroxy fatty acids and α,ω-dicarboxylic acids with carbon chain lengths from C14 to C22.

4. The method as claimed in claim 3, wherein the fatty acid is transformed in a biocatalytic step to the respsective ω-hydroxy or ω-carboxy ricinoleic analog or to a mixture of ω-hydroxy and ω-carboxy ricinoleic analogs.

5. The method as claimed in claim 3, wherein the w-hydroxy fatty acids and α,ω-dicarboxylic acids contain at least one additional functional group along fatty acid chains selected from the group consisting of alkenes, alkynes, conjugated alkenes, conjugated alkynes, ether, silicone, epoxy, quaternary ammonium salt, secondary amine, imine, and moieties including —S— and —P(X)—.

6. The method as claimed in claim 1, wherein the substrate is an alkyne.

7. The method as claimed in claim 1, wherein the substrate is a terminal alkene.

8. The method as claimed in claim 1, wherein the substrate is a partially hydrogenated cardanol.

9. The methods as claimed in claim 1, wherein the microorganism is selected from the group consisting of *Candida tropicalis*, *Candida cloacae*, *Cryptococcus neoforman*, and *Corynebacterium* sp.

10. The method as claimed in claim 1, wherein the fermentation process is divided into two phases, a growth phase and a transformation phase in which ω-oxidation of the substrate is performed.

11. The method as claimed in claim 1, wherein the seed culture is inoculated into the fermentation medium with elongated cultivation time at an increasing phase of pH after a minimum value.

12. The method as claimed in claim 11, wherein in the main fermentation stage, a steady state condition with a maximal active ingredient production rate is maintained for an extended period of time by:
(a) feeding of a carbon source and a nitrogen source to supply a nutrient demand;
(b) controlling glucose concentration;
(c) controlling stirring rate and aeration rate according to oxygen demand;
(d) maintaining a pH between the range of from about 5.2-6.2 with the feeding of the carbon source; and
(e) carrying out at least one withdrawals, when the maximal working volume of the fermenter is achieved, or when a mevinolin concentration economical enough to carry out downstream processing is reached.

13. The method as claimed in claim 1, wherein the pH is adjusted to about 7.5-8.0 by addition of a base solution and co-substrates can be fed during the transformation phase to provide energy for cell growth, whereby terminal methyl groups of the fatty acid, synthetically derived substrates, n-alkane, n-alkene, n-alkyne, and fatty alcohol that have carbon chain lengths from 12 to 22 are converted to hydroxyl or carboxyl groups.

14. The method as claimed in claim 13, wherein the w-hydroxy fatty acids and α,ω-dicarboxylic acids in fermentation broth are extracted and purified by:
(a) acidifying the liquid culture medium containing these products with concentrated hydrochloric acid to a pH of about 1.0~4.0 and extracted into diethyl ether;
(b) evaporating the solvent in ether extract under vacuum with a rotary evaporator; and
(c) further purifying the resulting product mixtures by silica gel column chromatography using silica gel, whereby chromatographic separations are conducted using an eluent that consists of a two-solvent system with solvents pairs selected so that one solvent is of low polarity while the other solvent is of higher polarity.

15. The method as claimed in claim 14, wherein ricinoleic acid analogs that have two carboxylic acids or have sufficient polarity to dissolve in alkaline medium are extracted and precipitated from fermentation broths by:
(a) adding an alkaline material to the fermentation broth and adjusting the pH of the solution to about 11-13 to dissolve dicarboxylic acids formed;
(b) adding a diatomaceous earth in an amount of about 2-8% by weight to the fermentation broth to selectively absorb lower polarity components of the mixture;
(c) filtering the fermentation broth under pressure by using a filter press and washing the filter cake at least 2 times with water;
(d) acidifying the obtained filtrate to a pH of 4.0 or below by adding an acid to precipitate dicarboxylic acid products; and
(e) further purifying the precipitated dicarboxylic acids by recrystallization using an organic solvent.

16. The method as claimed in claim 1, further comprising the step of using the ricinoleic acid analogs as monomers for oligomer and polymer synthesis.

17. The method as claimed in claim 16, wherein polymerizations of the monomers is carried out by chemical or enzymatic methods.

18. The method as claimed in claim 17, wherein the monomers are modified or converted to oligomers or polymers via enzymatic polymerizations using a lipase catalyst.

19. The method as claimed in claim 17, wherein the monomers are modified or converted to oligomers or polymers via enzymatic polymerizations using a cutinase catalyst.

20. The method as claimed in claim 17, wherein the monomers are modified or converted to oligomers or polymers via enzymatic polymerizations using an esterase catalyst.

21. The method as claimed in claim 17, wherein the monomers are modified or converted to oligomers or polymers via chemical polymerizations using tin octanoate or titanium alkoxides.

22. The method as claimed in claim 16, wherein the ricinoleic acid analogs are synthesized by oxidative biotransformation and then undergo a catalyzed homo- or co-polymerization using an enzyme that in nature functions for ester hydrolysis.

23. The method as claimed in claim 22, wherein the oxidative transformation is a yeast-catalyzed biotransformation.

24. The method as claimed in claim 22, wherein the enzyme is an immobilized enzyme catalyst.

25. The method as claimed in claim 22, wherein the enzyme is *Candida antarctica* lipase B.

26. The method as claimed in claim 22, wherein resulting polymers have a molecular weight of between about 20 000 and about 80 000 and a polydispersity of between about 20 and about 3.1.

27. A ricinoleic acid analog having a formula selected from the group consisting of:
1,18-cis-9-octadecenedioic acid;
1,22-cis-9-docosenedioic acid;
1,18-cis-9,12-octadecadienedioic acid;
12,18-dihydroxy-cis-9-octadecenoic acid;
7-hydroxy-cis-9-octadecenedioic acid;
cis-9,10-epoxy-1,18-octadecanedioic acid;
7-tetradecynedioic acid;
8-hexadecynedioic acid;
13,14-dihydroxytetradecanoic acid;
15,16-dihydroxyhexadecanoic acid;
17,18-dihydroxyoctadecanoic acid; and
ω-carboxyl cardanol, wherein the ricinoleic acid analog is produced from a process comprising the steps of:
a) cultivating a microorganism in a seed culture stage to produce an inoculum, wherein the microorganism is selected from the group consisting of microorganisms capable of producing P450 mono-oxygenase;
b) transferring the inoculum into a fermentation medium; and
c) maintaining growth stage conditions in a main fermentation stage to facilitate the catalysis of a substrate to ricinoleic acid analogs, wherein the main fermentation stage is maintained at a pH of between about 5.0 and 8.0 and a temperature of between about 22° C. and about 30° C. for a time period of between about 10-12 hours,
wherein the resulting ricinoleic acid analog has a formula selected from the group consisting of 1,18-cis-9-octadecenedioic acid; 1,22-cis-9-docosenedioic acid; 1,18-cis-9,12-octadecadienedioic acid; 7-hydroxy-1,18-cis-9-octadecenedioic acid; 12,18-dihydroxy-cis-9-octadecenoic acid; cis-9,10-epoxy-1,18-octadecanedioic acid; 7-tetradecynedioic acid; and 8-hexadecynedioic acid.

28. The ricinoleic analog as claimed in claim 27, wherein the microorgainsm is selected from the group consisting of *Candida tropicalis, Candida cloacae, Cryptococcus neoforman*, and *Corynebacterium* sp.

29. A polymer or oligomer produced from a catalyzed homo- or co-polymerization of a ricinoleic acid analog having a formula selected from the group consisting of:
1,18-cis-9-octadecenedioic acid;
1,22-cis-9-docosenedioic acid;
1,18-cis-9,12-octadecadienedioic acid;
12,18-dihydroxy-cis-9-octadecenoic acid;
7-hydroxy-cis-9-octadecenedioic acid;
cis-9,10-epoxy-1,18-octadecanedioic acid;
7-tetradecynedioic acid;
8-hexadecynedioic acid;
13,14-dihydroxytetradecanoic acid;
15,16-dihydroxyhexadecanoic acid;
17,18-dihydroxyoctadecanoic acid; and
ω-carboxyl cardanol,
wherein the ricinoleic acid analog is produced from the catalysis of a substrate selected from the group consisting of fatty acids, terminal alkenes, partially hydrogenated cardanol, and alkynes, and the catalysis uses a microorganism capable of producing enzymes capable of biotransforming the substrate, and
wherein the homo- or co-polymerization uses an enzyme that in nature functions for ester hydrolysis, and
wherein the ricinoleic acid analog is produced from a process comprising the steps of:
a) cultivating a microorganism in a seed culture stage to produce an inoculum, wherein the microorganism is selected from the group consisting of microorganisms capable of producing P450 mono-oxygenase;
b) transferring the inoculum into a fermentation medium; and
c) maintaining growth stage conditions in a main fermentation stage to facilitate the catalysis of a substrate to ricinoleic acid analogs, wherein the main fermentation stage is maintained at a pH of between about 5.0 and 8.0 and a temperature of between about 22° C. and about 30° C. for a time period of between about 10-12 hours,
wherein the resulting ricinoleic acid analog has a formula selected from the group consisting of 1,18-cis-9-octadecenedioic acid; 1,22-cis-9-docosenedioic acid; 1,18-cis-9,12-octadecadienedioic acid; 7-hydroxy-1,18-cis-9-octadecenedioic acid; 12,18-dihydroxy-cis-9-octadecenoic acid; cis-9,10-epoxy-1,18-octadecanedioic acid; 7-tetradecynedioic acid; and 8-hexadecynedioic acid.

30. The ricinoleic analog as claimed in claim 29, wherein the microorgainsm is selected from the group consisting of *Candida tropicalis, Candida cloacae, Cryptococcus neoforman*, and *Corynebacterium* sp.

31. The polymer or oligomer as claimed in claim 30, wherein the enzyme that in nature functions for ester hydrolysis is selected from the group consisting of lipases, cutinases, and esterases.

32. The polymer or oligomer as claimed in claim 31, wherein the lipase is *Candida antarctica* lipase B (CALB).

33. A polymer or oligomer produced from a catalyzed homo- or co-polymerization of a ricinoleic acid analog having a formula selected from the group consisting of:
1,18-cis-9-octadecenedioic acid;
1,22-cis-9-docosenedioic acid;
1,18-cis-9,12-octadecadienedioic acid;
12,18-dihydroxy-cis-9-octadecenoic acid;
7-hydroxy-cis-9-octadecenedioic acid;
cis-9,10-epoxy-1,18-octadecanedioic acid;
7-tetradecynedioic acid;
8-hexadecynedioic acid;
13,14-dihydroxytetradecanoic acid;
15,16-dihydroxyhexadecanoic acid;
17,18-dihydroxyoctadecanoic acid; and
ω-carboxyl cardanol,
wherein the homo- or co-polymerization uses a chemical catalyst, and
wherein the ricinoleic acid analog is produced from a process comprising the steps of:
a) cultivating a microorganism in a seed culture stage to produce an inoculum, wherein the microorganism is selected from the group consisting of microorganisms capable of producing P450 mono-oxygenase;
b) transferring the inoculum into a fermentation medium; and
c) maintaining growth stage conditions in a main fermentation stage to facilitate the catalysis of a substrate to ricinoleic acid analogs, wherein the main fermentation stage is maintained at a pH of between about 5.0 and 8.0 and a temperature of between about 22° C. and about 30° C. for a time period of between about 10-12 hours,
wherein the resulting ricinoleic acid analog has a formula selected from the group consisting of 1,18-cis-9-octadecenedioic acid; 1,22-cis-9-docosenedioic acid; 1,18-cis-9,12-octadecadienedioic acid; 7-hydroxy-1,18-cis-9-octadecenedioic acid; 12,18-dihydroxy-cis-9-octadecenoic acid; cis-9,10-epoxy-1,18-octadecanedioic acid; 7-tetradecynedioic acid; and 8-hexadecynedioic acid.

34. The ricinoleic analog as claimed in claim 33, wherein the microorgainsm is selected from the group consisting of *Candida tropicalis, Candida cloacae, Cryptococcus neoforman*, and *Corynebacterium* sp.

35. The polymer or oligomer as claimed in claim 34, wherein the chemical catalyst is tin octanoate or titanium alkoxides.

36. A method for producing ricinoleic acid analogs comprising the steps of:
a) cultivating a microorganism in a seed culture stage to produce an inoculum, wherein the microorganism is selected from the group consisting of microorganisms capable of producing P450 mono-oxygenase;

b) transferring the inoculum into a fermentation medium; and c) maintaining growth stage conditions in a main fermentation stage to facilitate the catalysis of a substrate to ricinoleic acid analogs, wherein the main fermentation stage is maintained at a pH of between about 5.0 and 8.0 and a temperature of between about 22° C. and about 30° C. for a time period of between about 10-12 hours, and wherein the substrate is selected from the group consisting of fatty acids, terminal alkenes, partially hydrogenated cardanol, and alkynes, and the catalysis uses a microorganism capable of producing enzymes capable of biotransforming the substrate, wherein the resulting ricinoleic acid analog has a formula selected from the group consisting of 1,18-cis-9-octadecenedioic acid; 1,22-cis-9-docosenedioic acid; 1,18-cis-9,12-octadecadienedioic acid; 7-hydroxy-1,18-cis-9-octadecenedioic acid; 12,18-dihydroxy-cis-9-octadecenoic acid; cis-9,10-epoxy-1,18-octadecanedioic acid; 7-tetradecynedioic acid; and 8-hexadecynedioic acid.

37. The method as claimed in claim 36, wherein the microorganism is selected from the group consisting of *Candida tropicalis, Candida cloacae, Cryptococcus neoforman*, and *Corynebacterium* sp.

38. The method as claimed in claim 36, wherein the fermentation process is divided into two phases, a growth phase and a transformation phase in which ω-oxidation of the substrate is performed, and the seed culture is inoculated into the fermentation medium with elongated cultivation time at an increasing phase of pH after a minimum value.

* * * * *